(12) United States Patent
Sherman

(10) Patent No.: US 6,656,503 B1
(45) Date of Patent: Dec. 2, 2003

(54) PHARMACEUTICAL TABLET COMPRISING AN NSAID AND MISOPROSTOL

(75) Inventor: Bernard Charles Sherman, 50 Old Colony Road, Willowdale Ontario (CA), M2L 2KI

(73) Assignee: Bernard Charles Sherman, Toronto (CA)

( * ) Notice: Subject to any disclaimer, the term of this patent is extended or adjusted under 35 U.S.C. 154(b) by 0 days.

(21) Appl. No.: 09/614,135

(22) Filed: Jul. 11, 2000

(30) Foreign Application Priority Data

Jul. 14, 1999 (CA) .............................. 2277407

(51) Int. Cl.[7] .............................. A61K 9/28; A61K 9/20
(52) U.S. Cl. .................. 424/474; 424/464; 424/465; 424/471; 424/484
(58) Field of Search ................................. 424/464, 489, 424/475, 480, 465, 471, 472, 474, 484

(56) References Cited

U.S. PATENT DOCUMENTS

| 4,301,146 A | 11/1981 | Sanvordeker |
| 5,601,843 A | 2/1997 | Gimet et al. |
| 5,800,836 A | * 9/1998 | Morella et al. ............. 424/489 |

* cited by examiner

Primary Examiner—Thurman K. Page
Assistant Examiner—Robert M. Joynes
(74) Attorney, Agent, or Firm—Neil H. Hughes; Ivor M. Hughes; Marcelo K. Sarkis

(57) ABSTRACT

A pharmaceutical tablet comprising a core and a film coating wherein the core comprises an NSAID and the film coating comprises a polymer and misoprostol.

20 Claims, No Drawings

PHARMACEUTICAL TABLET COMPRISING AN NSAID AND MISOPROSTOL

BACKGROUND OF THE INVENTION

The invention herein is directed to a pharmaceutical tablet which comprises both an NSAID and misoprostol.

Nonsteroidal anti-inflammatory drugs (NSAIDs) comprise a class of drugs which have therapeutic value especially for the treatment of inflammatory conditions such as exhibited in inflammatory diseases like osteoarthritis and rheumatoid arthritis. While the NSAIDs present a beneficial therapeutic value, they also exhibit an undesirable ulcerogenic effect generally associated with chronic use. NSAID induced ulcers in the stomach can be dangerous. Such ulcers generally exhibit few or no symptoms and may cause bleeding when undetected. In some instances, bleeding ulcers can prove fatal.

Certain prostaglandins have been shown to prevent NSAID induced ulcers. Misoprostol is a prostaglandin which has been accepted for use in the treatment of NSAID induced ulcers in many countries, including the United States.

It is desirable to provide a pharmaceutical composition which exhibits the beneficial properties of an NSAID and which also exhibits the beneficial properties of misoprostol for countering the ulcerogenic side effects attendant to NSAID administration.

This can be achieved by combining an NSAID and misoprostol in a single pharmaceutical tablet. However, this is not easy to do, because misoprostol is highly unstable, and it is thus desirable not to have the misoprostol and NSAID mixed together, so as to prevent any deleterious effect of the NSAID on the stability of the misoprostol.

One solution to this problem, which is disclosed in U.S. Pat. No. 5,601,843, is to produce a composition in the form of a tablet comprising within it a smaller tablet. Such a composition is known in the art as a "compression coated" tablet or "mantle" tablet. The portion of the larger tablet (i.e. the whole composition) that surrounds the smaller inner or "core" tablet is known as the "mantle". In the compositions of U.S. Pat. No. 5,601,843, the misoprostol and NSAID are separated from each other by having the core tablet comprise the NSAID and the mantle comprise the misoprostol.

It is also disclosed that, in order to prevent contact between the misoprostol and the NSAID at the surface of the inner core, the inner core may be coated with an inert film coating. Such coating may be an enteric film coating, which also serves to reduce the likelihood of the NSAID dissolving in the stomach and thereby prevent exposing the stomach to the NSAID.

While the invention of U.S. Pat. No. 5,601,843 accomplishes its objective of separating the NSAID from the misoprostol, it has certain disadvantages.

One disadvantage is that the process of making the mantle tablet is complicated, and the machinery needed is specialized and relatively expensive. In the process of manufacture of the mantle tablet, it is necessary to first make the smaller core tablet, which is done on a conventional tablet press, and then to use a compression coating press to make the final tablet. Such a press makes the final tablet much the same as a conventional tablet is made, but must have the added feature of being able to insert the core tablet along with the mantle powder mix into each die for compression into the final tablet.

Another disadvantage is that the final tablet must be substantially larger than the inner core tablet to have an adequate quantity of compressible mantle material completely surrounding the inner core. In the compositions of U.S. Pat. No. 5,601,843, the substantial mass of the mantle is in any event necessary to comprise the misoprostol. This is because misoprostol is unstable in pure form, and the only way known in the art to stabilize misoprostol is to process it into a dispersion comprising 1 part misoprostol in from about 50 to about 500 parts of a polymer, as disclosed in U.S. Pat. No. 4,301,146. The examples of U.S. Pat. No. 5,601,843 all use a dispersion of 1 part misoprostol in 100 parts hydroxypropyl methylcellulose ("HPMC"). Also this dispersion must be mixed with a binder, lubricant and other ingredients to make a mixture which can be compressed into the mantle. Thus it follows that the mass of the mantle must be large relative to the core.

In all nine examples of U.S. Pat. No. 5,601,843, the core tablet has a mass of 90 mg and the mantle has a mass of 265 mg. The nine examples differ from each other only in details of film coatings applied to the core tablet before it is inserted into the final tablet. Hence, in all nine examples, the total mass of the final tablet is at least 355 mg, despite the fact that the mass of the core tablet is only 90 mg.

The object of the present invention is to enable a pharmaceutical tablet that incorporates both an NSAID and misoprostol, but overcomes these disadvantages.

BRIEF SUMMARY OF THE INVENTION

The present invention is a pharmaceutical composition in the form of a tablet comprising a core and a film coating applied over the core, wherein the core comprises an NSAID and the film coating comprises misoprostol.

As aforesaid, the misoprostol must be stabilized by processing it into a dispersion in a polymer. However, a film coating also must comprise a polymer. The essence of the invention is to film-coat the core tablet with a coating comprised of both the misoprostol and a polymer, so that the polymer simultaneously serves the two purposes of stabilizing the misoprostol and forming a polymeric film coating around the core.

The procedure of applying the film coating comprising misoprostol is to dissolve the misoprostol and polymer in solvent, optionally along with other ingredients such as plasticizers and surfactants, and to spray the solution onto the tablets in conventional tablet coating equipment. As the solvent is evaporated, the film coating comprising the misoprostol and polymer is formed around the tablet.

DETAILED DESCRIPTION OF THE INVENTION

The NSAID contained within the core tablet will preferably be piroxicam, or diclofenac, or a salt of diclofenac, such as diclofenac sodium or diclofenac potassium. Most preferably, the NSAID will be diclofenac sodium.

Where diclofenac or a salt thereof is used, the amount per tablet will preferably be from about 25 to about 75 mg. The core tablet containing diclofenac or salt thereof will contain, along with the diclofenac or salt thereof, usual tablet excipients such as binders, lubricants, fillers and the like. Preferably, the tablet containing the diclofenac or salt thereof will be coated with an enteric film coating to prevent the diclofenac or salt thereof from dissolving until after it has passed through the stomach and entered the small intestine. The enteric coating can be formulated with any suitable enteric coating polymer, many of which are known to those skilled in the art.

Where piroxicam is used as the NSAID, the amount per tablet will preferably be from about 10 to about 20 mg. Again, the tablet containing piroxicam will also comprise usual tablet excipients.

It will be understood that the film coating comprising misoprostol may be sprayed directly on the core tablet containing the NSAID. Optionally, the core tablet may first be coated with an enteric film coating, and the film coating comprising the misoprostol applied as an overcoat.

Also optionally, the core tablet may first be coated with an enteric film coating and then overcoated with another inert film coating, and then overcoated again with the film coating comprising misoprostol.

Also optionally, another inert film coating may be applied on top of the film coating which comprises the misoprostol, in order to protect the misoprostol from the effects of light and air.

The polymer used in the film coating which comprises the misoprostol may be any water-soluble polymer which will form a film coating when sprayed onto a tablet and which will also stabilize misoprostol. The polymer will preferably be selected from povidone and water-soluble cellulose derivatives, and most preferably will be hydroxypropyl methylcellulose. The ratio of polymer to misoprostol by weight will preferably be from about 10 to about 100 parts polymer to 1 part misoprostol, and more preferably from about 15 to about 50 parts polymer to 1 part misoprostol.

The solvent system used to dissolve the misoprostol and polymer may be comprised of water or organic solvents and will preferably be a mixture of a chlorinated hydrocarbon and an alcohol, and most preferably be a mixture of methylene chloride and an alcohol. The solution will optionally also comprise other ingredients, such as a plasticizer or surfactant.

The invention will be further understood from the following example, which is intended to be illustrative and not limiting of the invention.

EXAMPLE 1

Core tablets are made with ingredients per tablet as follows:

|  | mg per tablet |
| --- | --- |
| diclofenac sodium | 50.0 |
| lactose (monohydrate) | 13.0 |
| microcrystalline cellulose | 12.9 |
| corn starch | 8.4 |
| povidone | 4.8 |
| magnesium stearate | 0.9 |
|  | 90.0 |

The process of production of these core tablets is to mix all of the ingredients except the magnesium stearate, granulate by adding water and mixing, dry the granules, add the magnesium stearate, mix again, and compress this final mixture into tablets on a tablet press.

These core tablets are then enteric coated by applying a coating with ingredients per tablet as follows:

|  | mg per tablet |
| --- | --- |
| cellulose acetate phthalate | 5.4 |
| diethyl phthalate | 1.5 |
|  | 6.9 |

The process of application of this film coating is to dissolve the cellulose acetate phthalate and the diethyl phthalate in acetone, and to spray the solution onto the tablets in a coating pan and evaporate the acetone.

These enteric film coated tablets are then overcoated with a film coating comprising hydroxypropyl methylcellulose, polyethylene glycol as plasticizer, and misoprostol, with the following ingredients per tablet:

|  | mg per tablet |
| --- | --- |
| hydroxypropyl methylcellulose | 4.0 |
| polyethylene glycol | 0.2 |
| misoprostol | 0.2 |
|  | 4.4 |

The process of application of this film coating is to dissolve the hydroxypropyl methylcellulose, polyethylene glycol, and misoprostol in a mixture of methylene chloride and methanol, and to spray the solution onto the enteric coated tablets in a coating pan and evaporate the methylene chloride and methanol.

What is claimed is:

1. A pharmaceutical composition in the form of a tablet comprising a core and a thin solvent based film coating applied over the core, wherein the core comprises an NSAID and the film coating comprises a polymer and misoprostol, further comprising (i) an enteric coating applied between the core and the film coating comprising the polymer and misoprostol and (ii) and an inert overcoating applied over the enteric coating prior to applying the polymer and misoprostol coating, wherein the weight ratio of the solvent based thin film coating to the coated tablet is selected from the group of ratios comprising less than about 5%, less than about 10%, and less than about 50%.

2. The pharmaceutical composition of claim 1 further comprising an inert coating applied to the film coating comprising the polymer and misoprostol.

3. The composition of claim 1 wherein the NSAID is piroxicam or diclofenac or a salt thereof.

4. The composition of claim 1 wherein the NSAID is diclofenac sodium.

5. The composition of claim 1, wherein the polymer is povidone or a water soluble cellulose derivative.

6. The composition of claim 1, wherein the polymer is hydroxypropyl methycellulose.

7. The composition of claim 1 wherein the ratio of polymer to misoprostol by weight is from about 10:1 to about 100:1.

8. The composition of claim 1 wherein the ratio of polymer to misoprostol by weight is from about 15:1 to about 50:1.

9. A process of making a pharmaceutical composition comprising the steps of making a core tablet comprising an NSAID, and applying around the core a film coating comprising a polymer and misoprostol by dissolving the polymer and misoprostol in solvent, spraying the solution on said core, evaporating the solvent and subsequently applying an inert coating to said film coating, wherein the weight ratio of the solvent based thin film coating to the coated tablet is selected from the group of ratios comprising less than about 5%, less than about 10%, and less than about 50%.

10. A process of making a pharmaceutical composition comprising the steps of making a core tablet comprising an NSAID, applying an enteric coating around the core, and applying an overcoating around the enteric coating comprising a polymer and misoprostol by dissolving the polymer and misoprostol in solvent, spraying the solution, and evaporating the solvent, wherein the weight ratio of the solvent based thin film coating to the coated tablet is selected from the group of ratios comprising less than about 5%, less than about 10%, and less than about 50%.

11. A process of claim 9 or 10 wherein the solvent comprises a chlorinated hydrocarbon and an alcohol.

12. A process of claim 10 wherein an inert coating is applied subsequently to said film coating.

13. A pharmaceutical composition in the form of a tablet comprising a core and a thin solvent based film coating applied over the core, wherein the core comprises an NSAID and the film coating comprises a polymer and misoprostol, and further comprising an inert coating applied to the film coating comprising the polymer and misoprostol, wherein the weight ratio of the solvent based thin film coating to the coated tablet is selected from the group of ratios comprising less than about 5%, less than about 10%, and less than about 50%.

14. The pharmaceutical composition of claim 13 further comprising an enteric coating applied between the core and the film coating comprising the polymer and misoprostol.

15. The pharmaceutical composition of claim 13 or 14 further comprising an inert overcoating applied over the enteric coating prior to applying the polymer and misoprostol coating.

16. A pharmaceutical composition in the form of a tablet comprising a core and a thin solvent based film coating applied over the core, wherein the core comprises an NSAID and the film coating comprises a polymer and misoprostol, wherein the weight ratio of the solvent based thin film coating to the coated tablet is selected from the group of ratios comprising less than about 5%, less than about 10%, and less than about 50%.

17. A process of making a pharmaceutical composition comprising the steps of making a core tablet comprising an NSAID, applying an enteric coating around the core, and applying an overcoating around the enteric coating comprising a polymer and misoprostol by dissolving the polymer and misoprostol in solvent, spraying the solution, and evaporating the solvent, wherein the weight ratio of the solvent based thin film coating to the coated tablet is selected from the group of ratios comprising less than about 1:20 and, less than about 1:10 thereby achieving a significantly smaller tablet to facilitate easier swallowing wherein the solvent comprises a chlorinated hydrocarbon and an alcohol.

18. A process of making a pharmaceutical composition comprising the steps of making a core tablet comprising an NSAID, applying an enteric coating around the core, and applying an overcoating around the enteric coating comprising a polymer and misoprostol by dissolving the polymer and misoprostol in solvent, spraying the solution, and evaporating the solvent, wherein the weight ratio of the solvent based thin film coating to the coated tablet is selected from the group of ratios comprising less than about 1:20 and, less than about 1:10 thereby achieving a significantly smaller tablet to facilitate easier swallowing wherein an inert coating is applied subsequently to said film coating.

19. A process of claim 18 wherein the solvent comprises a chlorinated hydrocarbon and an alcohol.

20. A process of claim 17 wherein an inert coating is applied subsequently to said film coating.

* * * * *